US009446431B2

(12) United States Patent
Young

(10) Patent No.: US 9,446,431 B2
(45) Date of Patent: Sep. 20, 2016

(54) HYDROPHILIC COATINGS AND METHODS FOR COATING MEDICAL DEVICES WITH HYDROPHILIC COATINGS

(71) Applicant: Cook Medical Technologies LLC, Bloomington, IN (US)

(72) Inventor: Ronan T. Young, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 219 days.

(21) Appl. No.: 14/459,927

(22) Filed: Aug. 14, 2014

(65) Prior Publication Data
US 2015/0051556 A1 Feb. 19, 2015

Related U.S. Application Data

(60) Provisional application No. 61/866,324, filed on Aug. 15, 2013.

(51) Int. Cl.
| *A61K 36/00* | (2006.01) |
| *A61L 31/10* | (2006.01) |
| *B05D 7/00* | (2006.01) |
| *A61L 29/08* | (2006.01) |
| *A61L 29/14* | (2006.01) |
| *A61L 31/14* | (2006.01) |
| *C09D 105/00* | (2006.01) |

(52) U.S. Cl.
CPC ............... *B05D 7/54* (2013.01); *A61L 29/085* (2013.01); *A61L 29/145* (2013.01); *A61L 31/10* (2013.01); *A61L 31/145* (2013.01); *C09D 105/00* (2013.01); *A61K 36/00* (2013.01); *A61L 2400/10* (2013.01); *A61L 2420/02* (2013.01); *A61L 2420/08* (2013.01); *Y10T 428/31971* (2015.04)

(58) Field of Classification Search
CPC ...................................................... A61K 36/00
USPC ...................... 427/2.1–2.31, 2.28, 2.24, 2.25
See application file for complete search history.

(56) References Cited

U.S. PATENT DOCUMENTS

| 4,801,475 | A |   | 1/1989 | Halpern et al. |
| 4,840,941 | A |   | 6/1989 | Ueno et al. |
| 4,959,074 | A |   | 9/1990 | Halpern et al. |
| 5,023,114 | A |   | 6/1991 | Halpern et al. |
| 5,037,677 | A |   | 8/1991 | Halpern et al. |
| 5,100,879 | A | * | 3/1992 | Ueno ..................... A01N 43/16 424/405 |
| 5,891,530 | A |   | 4/1999 | Wright |
| 6,106,889 | A |   | 8/2000 | Beavers et al. |
| 6,187,369 | B1 |  | 2/2001 | Beavers |
| 6,271,001 | B1 |  | 8/2001 | Clarke et al. |
| 6,280,789 | B1 |  | 8/2001 | Rey et al. |
| 6,673,453 | B2 |  | 1/2004 | Beavers et al. |
| 7,314,511 | B2 |  | 1/2008 | Campbell et al. |
| 7,320,690 | B2 |  | 1/2008 | Beavers et al. |
| 7,968,614 | B2 |  | 6/2011 | Chudzik et al. |
| 8,241,656 | B2 |  | 8/2012 | Chudzik et al. |
| 8,624,077 | B2 | * | 1/2014 | Rosenberg ........ A61F 13/00008 602/42 |
| 2010/0015200 | A1 |  | 1/2010 | McClain et al. |
| 2012/0142793 | A1 |  | 6/2012 | Frey et al. |
| 2012/0323311 | A1 |  | 12/2012 | McClain et al. |

FOREIGN PATENT DOCUMENTS

| EP | 0 240 098 A2 | 10/1987 |
| EP | 0 285 357 A2 | 10/1988 |

OTHER PUBLICATIONS

Li et al. Excellent Lubricating Behavior of Brasenia schreberi Mucilage. Langmuir, 2012, 28(20) pp. 7797-7802. May 1, 2012.*
Li, Jinjin, et al., "Excellent Lubricating Behavior of *Brasenia schreberi* Mucilage," Langmuir 28:7797-7802 (2012).
Oryza Oil & Fat Chemical Co., Ltd., "Water Shield Extract," ver. 1.0 HS, 34 pages (Mar. 25, 2013).

* cited by examiner

Primary Examiner — Cachet Sellman
(74) Attorney, Agent, or Firm — Brinks Gilson & Lione; Ryan L. Marshall

(57) ABSTRACT

Medical device surfaces, for example a plastic catheter or metal guide wire, are disclosed with a lubricating coating made from *Brasenia schreberi* polysaccharide mucilage. The coated device surfaces may be prepared with a variety of techniques offering improved alternatives to conventional coatings.

12 Claims, No Drawings

HYDROPHILIC COATINGS AND METHODS FOR COATING MEDICAL DEVICES WITH HYDROPHILIC COATINGS

FIELD OF THE INVENTION

The present invention generally relates to a method for producing a medical device with a hydrophilic surface coating. Specifically, the method is suitable for producing sterile medical devices which present a substrate, such as an elongate shaft, having an outer hydrophilic surface coating, such as a catheter for insertion into a passageway in a human or animal body.

BACKGROUND OF THE INVENTION

Plastic and metallic components are frequently used in medical devices. The material used for those components are often chosen with one or more material properties required for the function of the component, such as high flexural modulus, high tensile and compressive strength, or capacity to be shaped into useful forms. Those component materials, however, are frequently water-insoluble and hydrophobic, so that they are poorly wetted by water. Thus, water tends to form beads on the surface, or the material can sometimes act as a site for inflammatory responses or other undesirable biological outcomes. In addition, body implants, such as orthopedic joints and other bone replacements, often present problems with subnormal lubrication as the body recovers from the trauma of disease and its corrective treatment.

A number of polymer-based lubricious agents have been used to ameliorate the unwanted side effects arising from biologically incompatible materials. These polymer-based agents, however, are increasingly the suspected cause of detrimental effects when they slough off of a coated device in a patient. In addition, some coatings require a long and multi-step process to be applied to a substrate. Moreover, often these coatings have shortcomings and fail to provide lasting or effective relief to the undesirable side effects of the incompatible material. There remains, therefore, a need to provide alternative materials for coating medical device components that impart better lubricity, wettability, and biocompatibility.

SUMMARY OF THE INVENTION

In one aspect, a method of coating a medical device is disclosed, comprising (a) applying a *Brasenia schreberi* polysaccharide mucilage to a substrate; and (b) curing the polysaccharide mucilage.

In some embodiments, curing the polysaccharide includes applying ultraviolet light. In some embodiments, curing the polysaccharide includes adding a chemical curing agent selected from methanol, ethanol, and isopropyl alcohol.

In another aspect, a method of hydrophilic coating of normally hydrophobic surfaces is disclosed, comprising: (a) coating a hydrophobic surface with a *Brasenia schreberi* polysaccharide mucilage; (b) dehydrating water from the coating by applying a water-miscible solvent; (c) crosslinking and immobilizing the coating by applying a solution of catalyzed organic-soluble crosslinking agent.

In some embodiments, the water-miscible solvent is selected from ethanol, methanol, propanol, acetone, methyl ethyl ketone, tetrahydrofuan, dimethyl sulfoxide, acetonitrile, dimethylformamide, acetic acid, and mixtures of the same. In some embodiments, the crosslinking agent is acrylic monomer. In some embodiments, the method also includes applying a second *Brasenia schreberi* polysaccharide mucilage coating.

In another aspect, a medical article is disclosed and prepared from any of the methods described herein. In some embodiments, the article is selected from a wire guide, a catheter, and a drainage stent.

DETAILED DESCRIPTION

*Brasenia schreberi*, also known as water shield, is a ubiquitous aquatic plant with floating oval leaves and purple flowers, frequently found in lakes and slow-moving streams. It is often identified from its thick coating of gelatinous slime covering the young stems, buds, and the undersides of young leaves and generally of any submerged portion of the plant. The long reddish leaf stalks are attached to the centers of the floating oval leaves, giving them an umbrella-like appearance.

Water shield has been used as a food and as an astringent to treat abscesses and boils. It is also known to be anthelmintic and vulnerary. As mentioned above, the submerged parts of the plant are conspicuously covered in a mucilaginous jelly having polysaccharides. The jelly is a highly lubricious material that is not miscible in water at room temperature and is edible.

*Brasenia schreberi* mucilage is a polysaccharide believed to made from L-arabinose (about 5.9%), L-fucose (about 10.9%), D-galactose (about 34.1%), D-glucuronic acid (about 17.3%), D-mannose (about 13.4%), L-rhamnose (about 11.4%), and D-xylose (about 7.0%).

*Brasenia schreberi* as well as the mucilage from it is available from commercial sources such as Shenzhen Brasenia Schreberi Imp & Exp Co., Ltd (http://www.brasenia-schreberi.com) or Chongqing Eusinasia Foods Co., Ltd. (http://www.eusinasia.com; Chongqing, Chongqing, Longxi, Yubei District, Chongqing, China).

The mucilage can also be obtained by various techniques known to those of skill in the art. For example, the mucilage from *Brasenia schreberi* can be obtained by extraction. Extraction includes removing fluid from plant tissue by, for instance, physical or solvent-assisted means. An extract can be concentrated through commonly known methods, including evaporation of some or all of the volatile components of the fluid. For instance, if an extract has been made using a solvent-assisted method, it may be beneficial to subsequently remove some or all of the solvent. It will be clear to one of ordinary skill in the art that such a concentration process can be carried out until all volatile materials have been removed, leaving in a dry state elements of the original extract that were dissolved or suspended in the original fluid. This dried extract can then be comminuted by, for example, grinding to form a powder. Alternately, a spray drying technique as is known in the art can be used. In any case, the resultant powder can be re-solubilized in a polar solvent of choice, particularly water and certain organic solvents, and the resultant fluid generally will retain the lubricating characteristics of the original plant extract.

In some instances, it is possible to extract a fluid component from plant material by soaking the plant material in a solvent, for instance water or other polar solvents. Alternatively, a fluid component can be extracted from plant material by comminuting, crushing, squeezing, mashing, chopping, macerating, homogenizing, etc., the plant material thereby releasing a fluid component from insoluble plant tissue. It may be beneficial to perform this physical process with or in a solvent, for instance water or other polar solvents, in order to separate the desired fluid component more fully from insoluble plant material. Such insoluble plant material may include, for instance, seed hulls, cell wall fragments, vascular tissue, or fibers. In any of these processes, it may be beneficial to heat the plant tissue, solvent, or mixture thereof to aid in or accelerate the release of the fluid component.

Also, industrial processes that in some manner change the shape or form of a solid surface such as machining can be used to assist mucilage isolation.

Typically, mucilage can be obtained from plant product extracted from the plants through either physical means (e.g. crushing) and/or solvent-mediated means (e.g. extraction using water). Mucilage is a crude mixture comprising intra- and/or inter-cellular plant cell constituents. Though a predominant component of mucilage is often a heterogeneous collection of large glycans, it may also include other compounds, for instance simple carbohydrates, proteins, organic acids, or pigments. Individual components of mucilage may be either dissolved or suspended in a plant fluid base, depending upon the chemical characteristics and concentration of each component. If mucilage is extracted from plant tissue using solvent-assisted means, the resultant extract is referred to as mucilage extract.

In one embodiment, a hydrophilic coating is made from the water shield mucilage. The mucilage may be applied to or mixed with an acrylic monomer that is applied to a surface, such as a medical device component.

The acrylic monomers include monomers based on the structure of acrylic acid, which consists of a vinyl group and a carboxylic acid. Derivatives of aryclic acid may be used as well. Examples of acceptable acrylic monomers include: methyl methacrylate, acrylonitrile, methyl acrylate, ethyl acrylate, 2-chloroethyl vinyl ether, 2-ethylhexyl acrylate, hydroxyethyl methacrylate, butyl acrylate, butyl methacrylate, trimethylolpropane triacrylate.

Polymerization may be induced by adding a catalytic or higher amount of a photo initiator followed by exposure to a light source, such as a UV lamp. The photo initiator may be a compound is a compound that is activated by long-wavelength ultraviolet (UV) and visible light wavelengths. For example, the initiator includes a photoreducible or photo-oxidizable dye. Photoreducible dyes can also be used in conjunction with a compound such as a tertiary amine. The tertiary amine intercepts the induced triplet producing the radical anion of the dye and the radical cation of the tertiary amine. Examples of molecules exhibiting photosensitization reactivity and useful as an initiator include acridine orange, camphorquinone, ethyl eosin, eosin Y, erythrosine, fluorescein, methylene green, methylene blue, phloxime, riboflavin, rose bengal, thionine, and xanthine dyes.

In some embodiments, polymerization may be induced by adding a catalytic or higher amount of a thermally reactive initiator. Examples of thermally reactive initiators include 4,4' azobis(4-cyanopentanoic acid), 2,2-azobis[2-(2-imidazolin-2-yl)propane]dihydrochloride, and analogs of benzoyl peroxide.

In some embodiments, redox initiators can also be used to promote. In general, combinations of organic and inorganic oxidizers, and organic and inorganic reducing agents are used to generate radicals for polymerization. A description of redox initiation can be found in Principles of Polymerization 2nd Edition, Odian G., John Wiley and Sons, pgs 201-204, (1981).

In another embodiment, a hydrophilic coating is made from the water shield mucilage and a solvent to facilitate adhesion or reaction of the mucilage to a substrate surface. Examples of suitable solvents include ethanol, methanol, propanol, acetone, methyl ethyl ketone, tetrahydrofuan, dimethyl sulfoxide, acetonitrile, dimethylformamide, acetic acid, and mixtures of the same. The solvent can be removed by heat curing or chemical methods that react with any remaining water. For example, solvents such as methanol, ethanol, and isopropyl alcohol can be used to remove water from the substrate surface.

Examples of suitable substrates for the various techniques of applying the water shield mucilage include: wire guides, introducers, dilators, catheters, balloon catheters, drainage stents, and the like.

In another aspect, a method of coating a substrate surface of a medical device is disclosed. In the interest of clarity, it may be useful to consider stepwise the processes by which the novel plastic compositions of this invention may be produced, but it should be understood that the steps described are illustrative, rather than limiting.

The first step is to fabricate the object of interest, such as a bone- or joint-replacement, a catheter, wire guide, drainage stent, etc. These objects are made to normal specifications by conventional fabrication methods, such as injection molding, casting, compression molding, machining from billets, thermo-forming, etc. In the discussion that follows, the product of this first step will be termed the "structural part."

The second step may be to prepare the structural part to receive the polysaccharide coating. Since the structural part will usually be made from a highly hydrophobic material, it will often be desirable to apply a tie-coat which is less hydrophobic but still similar enough to wet and adhere well to the part. The tie-coat will also present a more wettable surface for the polysaccharide coating, so that the composite is more uniformly and securely cohering.

In the third step, the polysaccharide coating is applied, usually from water solution, by any suitable, conventional method, such as spraying, knife-coating, brushing, dipping, etc. Thickness of the wet film will depend upon the molecular weight and viscosity of the polysaccharide, but will usually be in the range of 30 to 500 mils. Multiple coats may be applied with intermediate drying periods, in order to build up the film thickness into the range noted.

The fourth step is to dehydrate the polysaccharide coating. This is done by intimately contacting the coated object with volatile non-solvents for the polysaccharide but miscible with water, which precipitate the polysaccharide onto the tie-coat or structural part and carry away the water. Suitable non-solvents may for example be lower aliphatic alcohols, such as methanol or ethanol, or mixtures of ethanol and diethyl ether. Any tendency of the polysaccharide coating to wrinkle in this treatment can be alleviated by spraying lightly with N-methylpyrrolidone as a leveling agent, or by adding a small amount of N-methylpyrrolidone or butyl acetate to the non-solvents used in the precipitation. The coating is now allowed to dry in a stream of clean air properly safeguarded against fire and explosion. This precipitation/drying treatment may need to be repeated. The purpose is to obtain a polysaccharide coating as free of water as possible.

The fifth step is to crosslink and/or graft the polysaccharide film to the tie-coat (if one has been used) and the tie-coat to the structural part. The polysaccharide must be insolubilized either by crosslinking or by grafting to the substrate; grafting to the structural part is an option depending upon how aggressive the conditions of service for the part will be.

Crosslinking can be accomplished in any of a variety of ways. The molecules of any polysaccharide chosen will contain hydroxyl groups through which crosslinking can be accomplished, for example with di- or polyisocyanates. *Brasenia schreberi* polysaccharide mucilage contains a plurality of carboxyl groups through which ionic crosslinking reactions are possible, for example with polyvalent cations. Chondroitin sulfate contains not only hydroxyls as reactive groups, but also acid sulfate groups.

The tie-coat can also be designed to participate in crosslinking and grafting reactions by containing similar reactive groups, as for example a solution copolymer comprising a major amount of methyl methacrylate and a minor amount of hydroxyethyl methacrylate or methacrylic acid.

In like manner, the structural part may be a copolymer comprising a minor amount of a monomer designed to introduce hydroxyl, carboxyl or other reactive groups.

Cross-linking can also dehydrate the polysaccharide coating because socyanates, diketenes, and other crosslinkers of choice may also react with any water that is present.

Optionally, the medical device is sterilized. Sterilization can be achieved by applying the proper combinations of heat, chemicals and/or irradiation. Heat sterilization can be performed in an autoclave, wherein steam is heated to 120-135 ° C. During chemical sterilization the medical device is for instance contacted with ethylene oxide (EtO), ozone or hydrogen peroxide. Sterilization by irradiation can, for instance, be performed by electron beam, x-ray or gamma ray irradiation.

The hydrophilic coating may comprise additives that protect the coating against a detrimental effect of radicals formed during sterilization. These additives are for example aliphatic compounds, alicyclic compounds and/or antioxidants. In principle any aliphatic stabilizing compound and/or alicyclic stabilizing compound may be used, in particular any such compound that is physiologically allowable and preferably non-toxic in the used concentration.

TEST METHODS

When the articles of this invention have been properly made, their treated surfaces are readily wettable (hydrateable) by water or saline solution and remain so in service unless damaged in ways that might rupture or forcefully remove the insoluble polysaccharide coating. Indeed, wetting behavior of the surface is itself a significant test method indicating qualitatively and in practical terms whether the polysaccharide surface is present and uniform. Since the film is clear and invisible to the unaided eye, test methods as means of confirming the continued presence and continuity of the coating under practical conditions of service can be helpful. One was named the "Hockey Puck Test" and a second the "Dye Retention Test." These are described briefly as follows.

The Hockey Puck Test

This test relies upon the fact that the water-wet polysaccharide film is more slippery than the tie-coat or the surface of the structural part. It is useful primarily on flat or nearly flat panels which have been equilibrated with water by submersion for an hour or more.

The panel to be tested is inserted horizontally in an open-sided box-like frame. The "puck" is a small aluminum lock with bottom surface freshly cleaned for each test. The block has a channel drilled horizontally into one side, connecting with a channel drilled vertically from the center of the top surface and internally threaded to receive an aluminum tube. Thin-walled rubber tubing is attached to this tube, with ample slack to provide for its free movement about the surface of the panel, leading to an on-off valve in a constant-pressure airline. The air pressure has been set at a level found by experience to cause ready sliding over a freshly prepared surface, but too low to cause sliding over the surfaces of tie-coat or structural part. If desired, the course of the puck can be guided to areas of special interest with a small rod in an experienced hand. In random movement over the panel surface, the puck will soon come to rest on any area that is bare due to improper preparation or to disruption in service.

The Dye Retention Test

This test requires that the polysaccharide film contain acidic functional groups such as carboxyls or acid. The test may be thwarted by conversion in service of the acidic groups to salts of common cations such as calcium or iron, so that negative results should be taken to mean simply that the test is significant only with other evidence that the polysaccharide film is no longer present.

The panel to be tested is immersed in an aqueous solution (0.05%) of Crystal Violet, a commercial dye, for one hour. It is transferred to a stirred rinse-bath for one hour and then allowed to drain for ten minutes. In the case of flat plastic panels, samples of appropriate size can be mounted in a standard colorimeter and the color intensity characterized on a numerical scale. Such values can then be related in a significant way to exposure to service conditions that the sample has been given.

Alternatively, such panel samples can be adapted in size and shape to examination in a spectrophotometer and characteristic peak absorbencies compared before and after real or simulated service exposures. While the dye salt may produce particularly strong absorbencies, especially in the ultraviolet, salt formation due to ion exchange in service can be confusing. Experience will show which absorbance frequency is most reliable as indicator in particular circumstances.

Friction Tester

The friction and durability of a coating on a device surface can be evaluated using a Harland FTS Friction Tester, available from Harland Medical Systems, with a clamp force for example of 100 g and a pull speed of 1.0 cm/s.

The invention claimed is:

1. A method of coating a medical device, comprising:
   (a) applying a *Brasenia schreberi* polysaccharide mucilage to a substrate;
   (b) curing the polysaccharide mucilage.

2. The method of claim 1, wherein curing the polysaccharide includes applying ultraviolet light.

3. The method of claim 1, wherein curing the polysaccharide includes adding a chemical curing agent selected from methanol, ethanol, and isopropyl alcohol.

4. A method of hydrophilic coating of normally hydrophobic surfaces, comprising:
   (a) coating a hydrophobic surface with a *Brasenia schreberi* polysaccharide mucilage;
   (b) dehydrating water from the coating by applying a water-miscible solvent;
   (c) crosslinking and immobilizing the coating by applying a solution of catalyzed organic-soluble crosslinking agent.

5. The method of claim 4, wherein the water-miscible solvent is selected from ethanol, methanol, propanol, acetone, methyl ethyl ketone, tetrahydrofuan, dimethyl sulfoxide, acetonitrile, dimethylformamide, acetic acid, and mixtures of the same.

6. The method of claims 4, wherein the crosslinking agent is acrylic monomer.

7. The method of claim 1, further comprising applying a second *Brasenia schreberi* polysaccharide mucilage coating.

8. The method of claim 5, further comprising applying a second *Brasenia schreberi* polysaccharide mucilage coating.

9. A medical article prepared from the method of claim 1.

10. The medical article of claim 9, wherein the article is selected from a wire guide, a catheter, and a drainage stent.

11. A medical article prepared from the method of claim 5.

12. The medical article of claim 11, wherein the article is selected from a wire guide, a catheter, and a drainage stent.

* * * * *